(12) United States Patent
Tollman

(10) Patent No.: US 9,326,916 B2
(45) Date of Patent: May 3, 2016

(54) NON-SPILL VALVE

(71) Applicant: BB IPR Limited, Middlesex (GB)

(72) Inventor: Stephen Paul Tollman, Middlesex (GB)

(73) Assignee: BB IPR Limited, Middlesex (GB)

( * ) Notice: Subject to any disclaimer, the term of this patent is extended or adjusted under 35 U.S.C. 154(b) by 0 days.

(21) Appl. No.: 14/361,598

(22) PCT Filed: Nov. 28, 2012

(86) PCT No.: PCT/GB2012/052931
§ 371 (c)(1),
(2) Date: May 29, 2014

(87) PCT Pub. No.: WO2013/079932
PCT Pub. Date: Jun. 6, 2013

(65) Prior Publication Data
US 2015/0020906 A1    Jan. 22, 2015

(30) Foreign Application Priority Data

Nov. 29, 2011 (GB) .................................. 1120545.7
Dec. 15, 2011 (GB) .................................. 1121532.4

(51) Int. Cl.
*A61M 39/24* (2006.01)
*A61J 11/00* (2006.01)
(Continued)

(52) U.S. Cl.
CPC ........... *A61J 11/002* (2013.01); *A47G 19/2272* (2013.01); *B65D 47/06* (2013.01);
(Continued)

(58) Field of Classification Search
CPC .............. A61J 11/0015; A61J 11/002; A61M 2039/2433; A61M 2039/242; A61M 2039/244

USPC ........... 215/11.4; 220/714; 137/844, 843, 855
See application file for complete search history.

(56) References Cited

U.S. PATENT DOCUMENTS 2,223,179 A   8/1937   Lougheed
4,179,051 A   12/1979  Thomas
(Continued)

FOREIGN PATENT DOCUMENTS

DE   29820894 U1   4/1999
DE   20019294 U1   5/2002
WO   01/97663 A1   12/2001

OTHER PUBLICATIONS

International Search Report dated Mar. 6, 2013 from corresponding International Application No. PCT/GB2012/052931; 4 pgs.
International Search Reporting dated Mar. 25, 2013 from corresponding Application No. GB11121532.4; 2 pgs.

*Primary Examiner* — Jeffrey Allen
*Assistant Examiner* — Jennifer Castriotta
(74) *Attorney, Agent, or Firm* — MacMillan, Sobanski & Todd, LLC

(57) ABSTRACT

A non-spill valve for the neck of a liquid container. The invention also relates to a non-spill valve for the nipple of a feeding bottle, to a teat which is provided with such a nipple and to a feeding bottle which has such a teat. The valve has a tube which is open at one end and upstands from a support, which is complementary with interior element so that it forms a partition and permits the passage of liquid from an aperture in the support only into the tube interior, wherein the other end of the tube is closed except for an incision which separates the closed end from an adjoining side wall portion. The incision defines a flap that can permit liquid to reach from the tube interior to the mouth of the neck or spout or nipple.

6 Claims, 4 Drawing Sheets

(51) Int. Cl.
*B65D 47/20* (2006.01)
*A47G 19/22* (2006.01)
*B65D 47/06* (2006.01)
*F16K 15/14* (2006.01)

(52) U.S. Cl.
CPC ............ *B65D47/2031* (2013.01); *F16K 15/14* (2013.01); *A61M 2039/242* (2013.01); *A61M 2039/244* (2013.01); *A61M 2039/2433* (2013.01); *Y10T 137/7879* (2015.04)

(56) References Cited

U.S. PATENT DOCUMENTS

| | | | |
|---|---|---|---|
| 5,035,340 A * | 7/1991 | Timmons | 215/11.4 |
| 6,325,236 B1 | 12/2001 | Wong | |
| 2001/0020623 A1* | 9/2001 | McDonough et al. | 220/714 |
| 2002/0063103 A1* | 5/2002 | Kiernan | 215/11.4 |
| 2005/0184075 A1* | 8/2005 | Belcastro | 220/714 |
| 2006/0108373 A1 | 5/2006 | Cheng | |

\* cited by examiner

NON-SPILL VALVE

The invention relates to a non-spill valve for the neck or spout of a liquid container, to a cap for the container in which the cap is provided with such a neck or spout and to a container which is fitted with such a cap, for example a so-called non-spill drinking cup for toddlers and incapacitated persons. The invention also relates to a non-spill valve for the nipple of a feeding bottle for babies and invalids, to a teat for the bottle in which the teat is provided with such a nipple and to a feeding bottle which is fitted with such a teat.

According to one aspect of the invention, the non-spill valve comprises a flexible tube which is open at one end and upstands from an apertured support of which the aperture is in registry with and of the same size as the open end of the tube, the support having a shape which is complementary with the interior of the neck or spout or nipple so that it forms a partition in the neck or spout or nipple of the container or feeding bottle and permits the passage of liquid from the aperture in the support only into the tube interior, wherein the other end of the tube is closed except for an incision which separates the closed end from an adjoining side wall portion of the tube, the incision being continued along said side wall portion up to a distance short of the support so as to define a flap which is hinged to the support wall and lies against the part from which it is severed but can flex under suction applied to the neck or spout or nipple and thereby permit liquid to reach from the tube interior to the mouth of the neck or spout or nipple.

Preferably, the material of the flexible tube is silicone and is moulded in one piece with its support. The support will be provided with at least one ridge or rib adapted to interengage with a groove or shoulder enabling the support and tube to be removably fixed in position within the neck or spout or nipple.

According to another aspect of the invention, the aforementioned spout or neck or nipple is likewise of flexible plastics material and moulded in one piece with at least one such non-spill flap valve and its support. If two or more flap valves are provided, there can be a single support with a corresponding number of complementary apertures for the tubes of the valves. Further, instead of being moulded in one piece with the cap of a container or with the teat of a feeding bottle, the or each tube may be moulded together with mounting means for connecting the spout or neck or nipple to a cap or teat of the container or feeding bottle.

Examples of the invention will now be described with reference to the accompanying drawings wherein.

Figure 1:
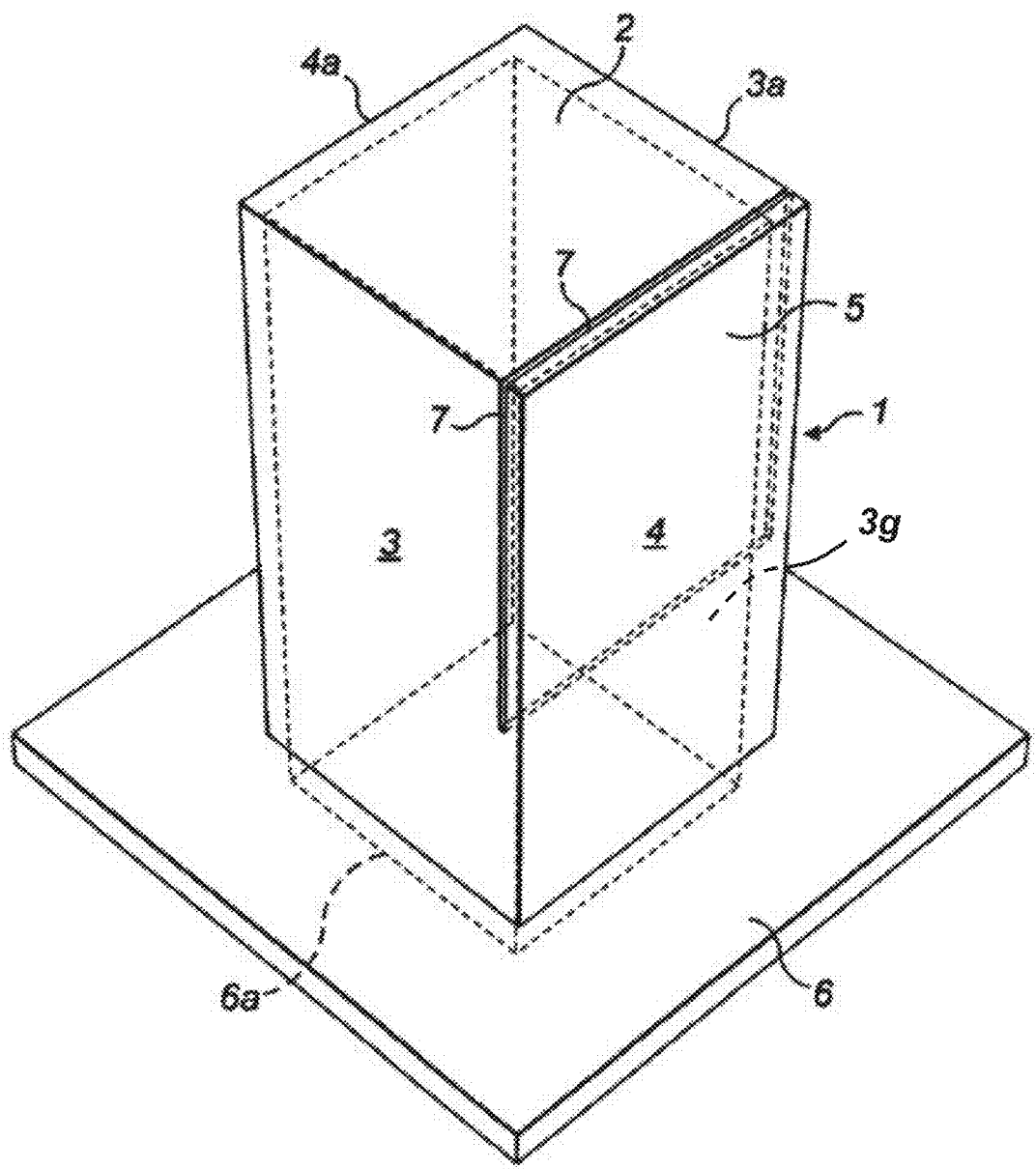
FIG. 1 is a diagrammatic pictorial view of a flap valve according to the invention.

Referring to FIG. 1, the flap valve comprises a tube 1 of substantially rectangular cross-section open at its lower end and closed at the top by a wall 2. The tube sides are defined by opposite side walls 3 and 3g and opposite side walls 4 and 4a.

The open lower end of the tube 1 is in registry with and of the same size as a hole 6a in a support 6 from which the tube 1 upstands and which is preferably moulded in one piece with the tube 1 from a flexible plastics material such as silicone. The side wall 4 is fully separated from the top wall 2 and partially separated from the side walls 3 and 3a by an incision 7 which stop short of the support 6 so as to define a flap 5 which is hinged to the lower part of the wall 4. By reason of the nature of the flexible silicone material, the flap 5 lies snugly against the edges of the walls 2, 3 and 3a from which it was severed.

When the valve of FIG. 1 is inserted in a spout or neck or nipple of a liquid container or nipple of a feeding bottle, or if it is moulded in one piece therewith, so that the closed top end of the tube 1 is directed towards the mouth of the spout or neck or towards the hole in the teat and the open lower end communicates with the liquid contents of the container or bottle through the aperture 6a in the support 6, liquid is prevented from reaching the mouth of the spout or neck or nipple by the tube being held shut by the flap 5. Consequently, no liquid can reach the mouth of the spout or neck or nipple. However, if vacuum is applied to the exterior of the tube wall 4 by suction being applied by the user, the flexibility of the silicone material will permit the flap portion 5 of the wall 4 to flex away from the walls 2, 3 and 3a of the tube to leave a gap through which liquid is sucked up from the container to the mouth of the spout or neck. When the user stops sucking, the memory characteristic of the silicone material of the flap causes it to flex back to the closing position against the walls 2, 3 and 3a.

Figure 2:
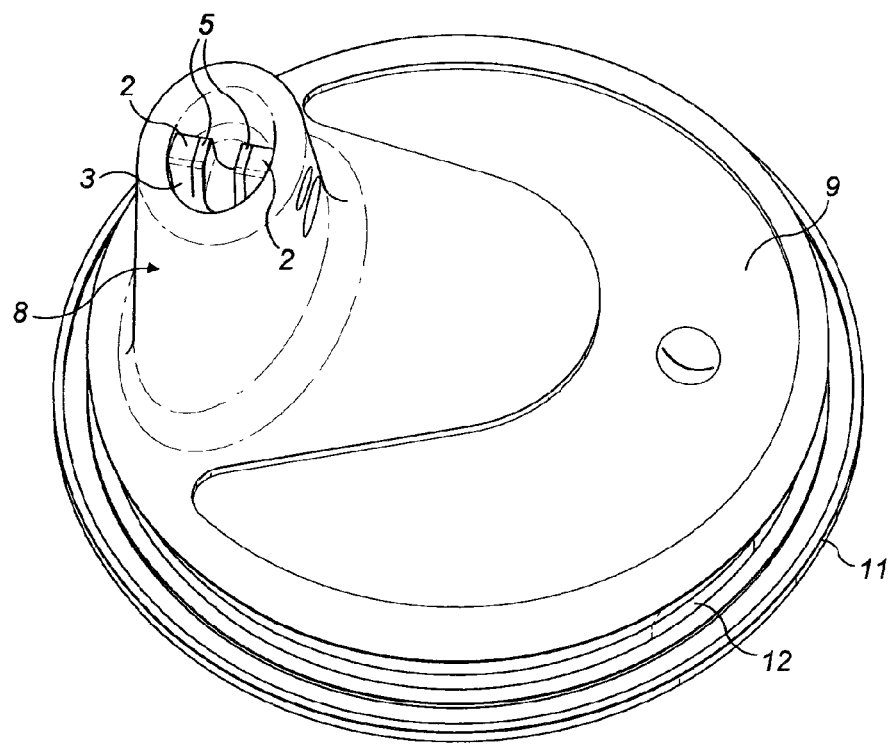
FIG. 2 is a pictorial view of part of a cap with spout for a non-spill mug, the spout of the cap being fitted with two flap valves.
Figure 3:
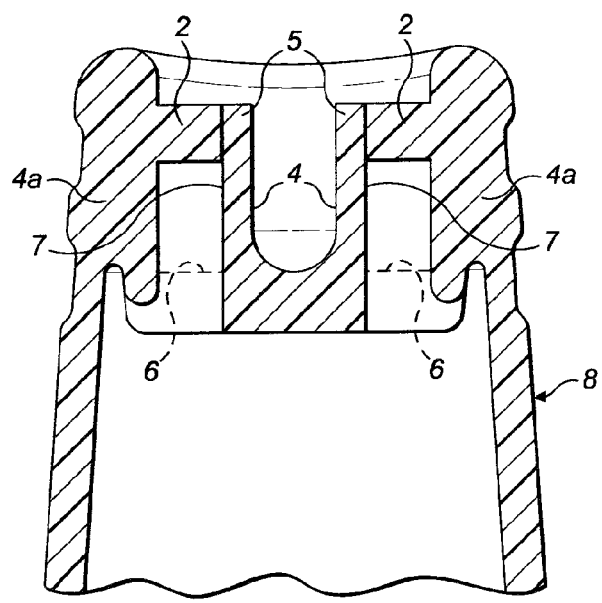
FIG. 3 is cross-sectional view of the FIG. 2 spout with the two non-spill valves moulded into it.

Referring to FIG. 2, this pictorial view illustrates part of a closure cap for a non-spill mug having an elliptical integral spout 8 of silicone material moulded to a silicone closure portion 9 which is part of the closure cap. The spout 8 contains two flap valves within the nozzle constructed in the manner described with reference to the FIG. 1 construction. Of course in this case, the support 6 which is shown in FIG. 1, not visible in FIG. 2 and shown in broken lines in: the: cross-section of FIG. 3 would be of elliptical shape and contain two apertures each to communicate with the lower open end of each tube.

Figure 6:
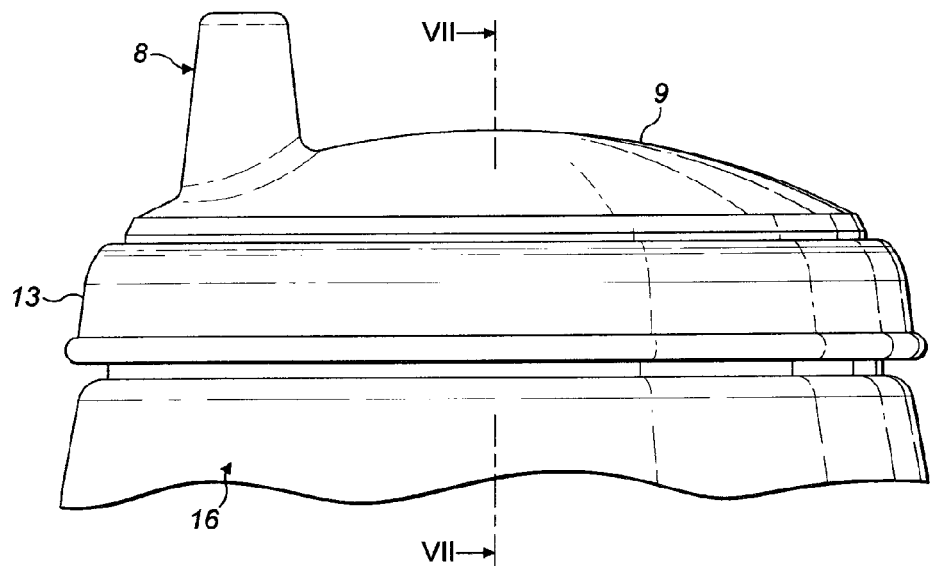
FIG. 6 is a fragmentary side elevation of a drinking cup or mug fitted with the FIG. 2 closure cap.
Figure 7:
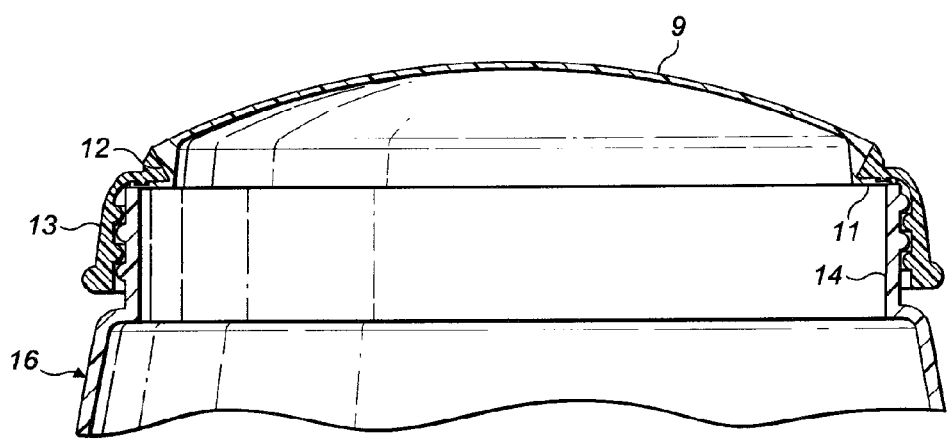
FIG. 7 is a fragmentary cross-section of the mug taken on the line VII-VII in FIG. 6.

The closure portion 9 is circular and at its circumference contains a shoulder 11 and groove 12 for inter-engagement with a less flexible or non-flexible ring shown in FIGS. 6 and 7 and having an internally screw threaded circular skirt 13 for engaging an externally screwthreaded neck 14 of a mug 16 in conventional manner. The silicone closure portion 9 therefore has its shoulder 11 sealingly trapped between the neck 13 of the mug 16 and the ring 13 of the closure cap.

Figure 4:
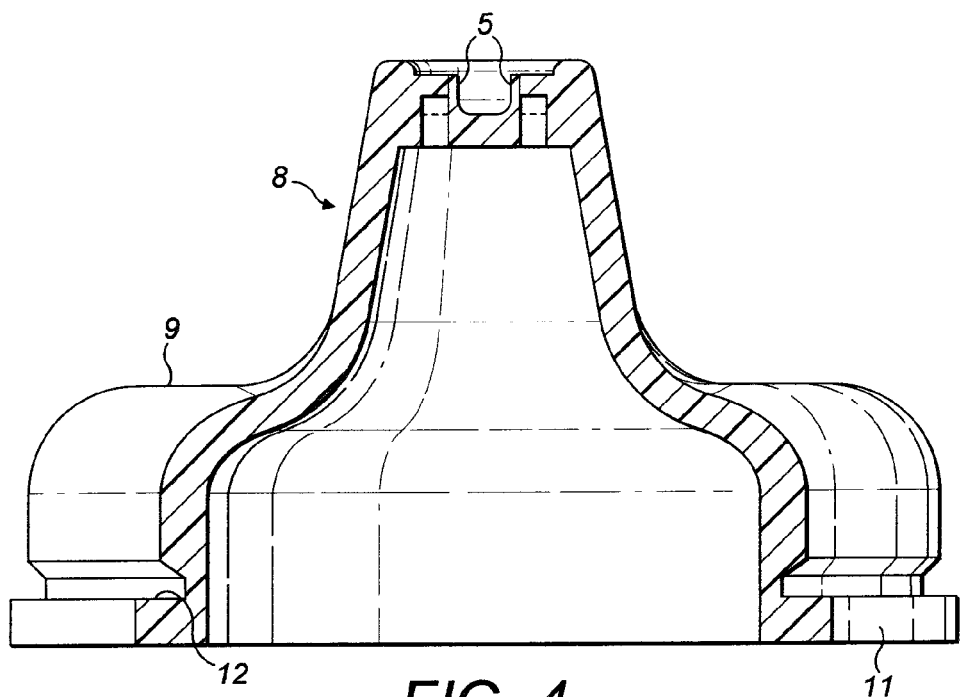
FIGS. 4 and 5 are cross-sectional views similar to FIG. 3 and showing the flap valves of a modified spout respectively in the closed and open conditions.
Figure 5:
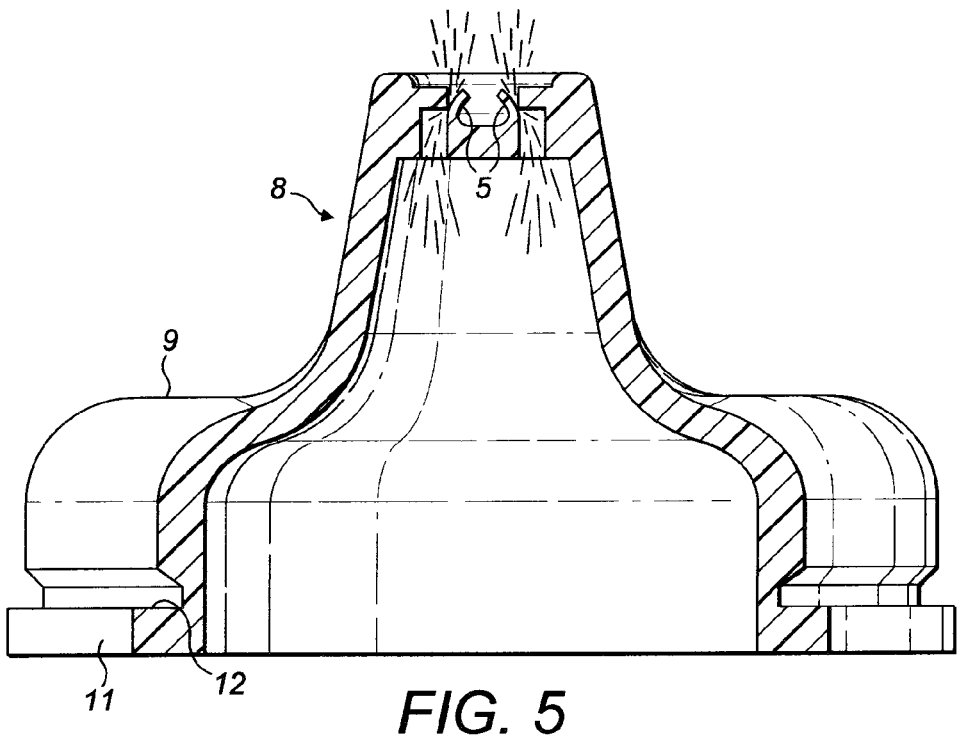

The cross-sectional views of FIGS. 4 and 5 of a modified spout have been included to show that the flaps 5 of the two valves are in the closed position of FIG. 4 when the user is not sucking on the spout 8 but will flex to the open position of FIG. 5 when the user of the mug sucks on the mouth of the spout 8.

It will be evident that the invention is applicable not only to the spouts of non-spill mugs but also other drinking vessels and in particular to the removable teats of feeding bottles.

The invention claimed is:

1. A non-spill valve for a neck and spout of a liquid container, comprising:
   a flexible tube which is open at a first end and upstands from an apertured support of which an aperture is in registry with and of the same size as the first open end of the tube, the support having a shape which is complementary with an interior of the neck and spout so that it forms a partition in the neck and spout of the container and permits the passage of liquid from the aperture in the support into the tube interior, wherein a second end of the tube directed towards a mouth of the neck or spout is closed and an incision separates a side wall portion of the tube from the second end and the adjoining portions of the side wall portions of the tube, wherein the incision continues along the side wall portion up to a distance short of the support to define a flap which is substantially perpendicular to the support and which is hinged to a remaining portion of the side wall portion, and wherein the flap lies against the second end and the adjoining portions of the side wall portions of the tube from which it is severed, and wherein the flap can flex under suction applied to the neck and spout and thereby permit liquid to reach from the tube interior to a mouth of the neck or spout.

2. A valve according to claim 1, wherein the material of the flexible tube is silicone and is moulded in one piece with its support.

3. A valve according to claim 2, wherein the spout and neck is flexible silicone material and moulded in one piece with at least one flap and its support.

4. A valve according to claim 3, comprising two tubes each with an associated flap and a single support having two apertures, one associated with each tube.

5. A valve according to claim 1, wherein the tube is moulded together with a silicon closure portion having mounting means for connecting the spout and neck to a cap ring of the container.

6. A nipple for a feeding bottle having a non-spill valve as claimed in claim 1, wherein the support has a shape which is complementary with the interior of the nipple so that it forms a partition in the nipple.

\* \* \* \* \*